United States Patent
Borini et al.

(10) Patent No.: US 9,080,928 B2
(45) Date of Patent: Jul. 14, 2015

(54) APPARATUS AND ASSOCIATED METHODS

(71) Applicant: Nokia Corporation, Espoo (FI)

(72) Inventors: Stefano Marco Borini, Cambridge (GB); Richard White, Huntingdon (GB); Elisabetta Spigone, Cambridge (GB); Michael Robert Astley, Cambridgeshire (GB); Di Wei, Cambridge (GB); Jani Kivioja, Cambridgeshire (GB); Teuvo Tapani Ryhanen, Helsinki (FI)

(73) Assignee: Nokia Technologies Oy, Espoo (FI)

( * ) Notice: Subject to any disclaimer, the term of this patent is extended or adjusted under 35 U.S.C. 154(b) by 279 days.

(21) Appl. No.: 13/739,518

(22) Filed: Jan. 11, 2013

(65) Prior Publication Data

US 2014/0196522 A1     Jul. 17, 2014

(51) Int. Cl.
  *G01N 5/02*     (2006.01)
  *G01N 7/00*     (2006.01)
  *G01K 1/00*     (2006.01)

(52) U.S. Cl.
  CPC ... *G01N 7/00* (2013.01); *G01K 1/00* (2013.01)

(58) Field of Classification Search
  CPC .................................................... G01N 25/00
  USPC ............................................. 73/25.04, 29.01
  See application file for complete search history.

(56) References Cited

U.S. PATENT DOCUMENTS 4,443,791 A * 4/1984 Risgin et al. ................ 73/23.21
4,795,968 A * 1/1989 Madou et al. ................. 422/88
5,841,021 A * 11/1998 De Castro et al. ............. 73/23.2
2005/0188764 A1* 9/2005 Itakura et al. ............... 73/335.04
2006/0246642 A1* 11/2006 Veeramma ................... 438/197

(Continued)

FOREIGN PATENT DOCUMENTS

JP    H02228546 A    9/1990
WO   WO-98-03857 A1  1/1998

(Continued)

OTHER PUBLICATIONS

Briand, D., et al., "Making Environmental Sensors on Plastic Foil", Materials Today, Sep. 2011, vol. 14, No. 9, © Elsevier Ltd. 2011, 8 pgs.

(Continued)

*Primary Examiner* — Laura Martin
*Assistant Examiner* — Alex Devito
(74) *Attorney, Agent, or Firm* — Harrington & Smith

(57) ABSTRACT

An apparatus including first and second sensor elements, the first sensor element includes a first sensor material. The second sensor element includes a second sensor material. The first sensor material is configured such that an electrical property of the first sensor material is dependent upon the temperature of the environment in which the first and second sensor elements are located. The second sensor material is configured such that the same electrical property of the second sensor material is dependent upon the relative vapor pressure of a fluid in the environment in which the first and second sensor elements are located, the respective temperature and fluid relative vapor pressure dependencies of the first and second sensor materials allowing the temperature and fluid relative vapor pressure of the environment to be determined based on combined measurements of the electrical property of the first and second sensor materials in the environment.

17 Claims, 10 Drawing Sheets

(56) References Cited

U.S. PATENT DOCUMENTS

2008/0054408 A1* 3/2008 Tippey et al. ............... 257/621
2011/0138882 A1* 6/2011 Moon et al. ................. 73/31.06
2012/0055815 A1* 3/2012 Truex et al. ................. 206/205

FOREIGN PATENT DOCUMENTS

WO WO-2012/178071 A2 12/2012
WO WO-2013/144788 A1 10/2013

OTHER PUBLICATIONS

Guo, L., et al., "Two-beam-laser interference mediated reduction, patterning and nanostructuring of grapheme oxide for the production of a flexible humidity sensing device", SciVerse ScienceDirect, © 2011 Elsevier Ltd., 7 pgs.

Jung, I., et al., "Tunable Electrical Conductivity of Individual Graphene Oxide Sheets Reduced at "Low" Temperatures", NANO letters, 2008. vol. 8, No. 12, © 2008 American Chemical Society, 5 pgs.

Kim, K.S., et al., "Large-scale pattern growth of grapheme films for stretchable transparent electrodes", Nature, vol. 457, Feb. 2009, © 2009 Macmillan Publishers Ltd., 5 pgs.

Lazzari, M., et al., "Block Copolymers as a Tool for Nanomaterial Fabrication", Advanced Materials, 2003, 15, No. 19, © 2003 Wiley-VCH Verlag GmbH & Co. KGaA, Weinheim, 12 pgs.

Nair, R.R., et al., "Unimpeded Permeation of Water through Helium-Leak-Tight Graphene-Based Membranes", Science, Jan. 27, 2012, vol. 335, 3 pgs.

Nair, R.R., et al., Supporting Online Material for: "Unimpeded Permeation of Water through Helium-Leak-Tight Graphene-Based Membranes", Science, published Jan. 27, 2012, www.seicncemag.org, 13 pgs.

Graphene Square Inc., www.graphenesq.com, graphene goods, Nov. 19, 2012, 1 pg.

Zyxio—Hardware and Software Solution, Home Applications Sensawaft, Media Company, Contact Terms, www.zyxio.com, Nov. 19, 2012, 1 pg.

Yao, Y., et al., "Humidity sensing behaviors of graphene oxide-silicon bi-layer flexible structure", Crown copyright © 2011 Published by Elsevier B.V., 6 pgs.

Yao, Y., et al., "The effect of ambient humidity on the electrical properties of grapheme oxide films", Nanoscale Research Letters, © 2012 Yao et al., licensee Springer, 7 pgs.

Cheng-Long Zhao et al.; "Enhanced Performance of a CMOS Interdigital Capacitive Humidity Sensor by Graphene Oxide"; 2011 16th International Solid-State Sensors, Actuators aand Microsystems Conference (Transducers 2011); Beijing, China; Jun. 5-9, 2011; pp. 1954-1957.

* cited by examiner

APPARATUS AND ASSOCIATED METHODS

TECHNICAL FIELD

The present disclosure relates to the field of environmental sensors, associated methods and apparatus, and in particular concerns a low-cost integrated sensor which is capable of measuring both the temperature and fluid relative vapour pressure of the surrounding environment. Certain disclosed example aspects/embodiments relate to portable electronic devices, in particular, so-called hand-portable electronic devices which may be hand-held in use (although they may be placed in a cradle in use). Such hand-portable electronic devices include so-called Personal Digital Assistants (PDAs) and tablet PCs.

The portable electronic devices/apparatus according to one or more disclosed example aspects/embodiments may provide one or more audio/text/video communication functions (e.g. tele-communication, video-communication, and/or text transmission, Short Message Service (SMS)/Multimedia Message Service (MMS)/emailing functions, interactive/non-interactive viewing functions (e.g. web-browsing, navigation, TV/program viewing functions), music recording/playing functions (e.g. MP3 or other format and/or (FM/AM) radio broadcast recording/playing), downloading/sending of data functions, image capture function (e.g. using a (e.g. in-built) digital camera), and gaming functions.

BACKGROUND

At present, low-cost integrated flexible temperature and humidity sensors are not available in the market. The apparatus and methods disclosed herein may or may not address this issue.

The listing or discussion of a prior-published document or any background in this specification should not necessarily be taken as an acknowledgement that the document or background is part of the state of the art or is common general knowledge. One or more aspects/embodiments of the present disclosure may or may not address one or more of the background issues.

SUMMARY

According to a first aspect, there is provided an apparatus comprising first and second sensor elements, the first sensor element comprising a first sensor material and the second sensor element comprising a second sensor material, wherein the first sensor material is configured such that an electrical property of the first sensor material is dependent upon the temperature of the environment in which the first and second sensor elements are located, and the second sensor material is configured such that the same electrical property of the second sensor material is dependent upon the relative vapour pressure of a fluid in the environment in which the first and second sensor elements are located, the respective temperature and fluid relative vapour pressure dependencies of the first and second sensor materials allowing the temperature and fluid relative vapour pressure of the environment to be determined based on combined measurements of the electrical property of the first and second sensor materials in the environment.

The term "relative vapour pressure" as used throughout the specification may be taken to mean the ratio between the partial vapour pressure of a fluid and its saturation vapour pressure at a given temperature.

The electrical property of the first sensor material may also be dependent upon the relative vapour pressure of the fluid in the environment. The electrical property of the second sensor material may also be dependent upon the temperature of the environment. The temperature and fluid relative vapour pressure dependencies of the first sensor material may be different from the temperature and fluid relative vapour pressure dependencies of the second sensor material.

The first sensor material may be different from the second sensor material. The first and second sensor materials may each comprise oxide materials. The oxide material of the first sensor material may have a different oxidation state than the oxide material of the second sensor material. The first sensor material may comprise one or more functional groups which are absent in the second sensor material. The first and second sensor materials may each comprise one or more functional groups. The one or more functional groups of the first sensor material may be different to the one or more functional groups of the second sensor material.

The first sensor element may comprise a passivation layer which is absent from the second sensor element. The passivation layer may be configured to prevent exposure of the first sensor material to the fluid in the environment. The passivation layer may comprise a fluoropolymer (such as Cytop™ by AGC Chemicals Europe Ltd).

The first and second sensor materials may each comprise a stack of pseudo two-dimensional platelets having an interstitial spacing. The interstitial spacing of the pseudo two-dimensional platelets in the first sensor material may be different from the interstitial spacing of the pseudo two-dimensional platelets in the second sensor material under the same environmental conditions.

The first and/or second sensor materials may comprise one or more of graphene, graphene oxide, boron nitride, fluorographene, hydrogenated graphene, tungsten disulphide and molybdenum disulphide.

One or more of the first and second sensor elements may comprise a protective layer configured to prevent damage to the first and second sensor materials, respectively. The protective layer may comprise a material which is permeable to the fluid in the environment to enable the prevention of damage to the sensor material without preventing the fluid relative vapour pressure of the environment from being determined. The protective layer may comprise a block co-polymer.

The fluid relative vapour pressure may provide an indication of the relative humidity of the environment. The fluid may comprise one or more of a liquid and a gas. The fluid may comprise water.

The first and second sensor elements may each comprise an electrode pair configured to enable a flow of alternating current through the respective sensor materials. The electrode pair of the first sensor element may comprise a different electrode geometry and/or electrode material from the electrode pair of the second sensor element. The electrode pair of the first and/or second sensor elements may comprise interdigitated comb electrodes, interpenetrating spiral electrodes or parallel plate electrodes. One or both of the parallel plate electrodes of the first and/or second sensor element may be configured to serve as a passivation layer and/or protective layer of the respective sensor element.

The electrical property may be one or more of impedance, resistance, conductance, reactance and capacitance. The apparatus may comprise one or more reference components (e.g. capacitors or resistors) configured to enable the electrical property (e.g. capacitance or resistance) of the first and second sensor materials to be measured as a ratio to the electrical property of the one or more reference components, respectively.

The apparatus may comprise a controller configured to receive the electrical property measurements of the first and second sensor materials and determine the temperature and fluid relative vapour pressure of the environment based on the received electrical property measurements. The apparatus may comprise an interface circuit configured to convert output signals from the first and second sensor elements into a form which is suitable for use by the controller. The interface circuit may comprise one or more of a voltage divider, a Wheatstone bridge, a phase-sensitive detection circuit, and an analogue-to-digital converter.

The apparatus may be one or more of an electronic device, a portable electronic device, a portable telecommunications device, a sensor, a wearable device, a wristband, a user interface for one or more of the same, an electronic display for one or more of the same, and a module for one or more of the same.

According to a further aspect, there is provided a method of determining the temperature and fluid relative vapour pressure of an environment using an apparatus, the apparatus comprising first and second sensor elements,
the first sensor element comprising a first sensor material and the second sensor element comprising a second sensor material, wherein the first sensor material is configured such that an electrical property of the first sensor material is dependent upon the temperature of the environment in which the first and second sensor elements are located, and the second sensor material is configured such that the same electrical property of the second sensor material is dependent upon the relative vapour pressure of a fluid in the environment in which the first and second sensor elements are located, the respective temperature and fluid relative vapour pressure dependencies of the first and second sensor materials allowing the temperature and fluid relative vapour pressure of the environment to be determined based on combined measurements of the electrical property of the first and second sensor materials in the environment, the method comprising measuring the electrical property of the first and second sensor materials and determining the temperature and fluid relative vapour pressure of the environment based on the combined electrical property measurements.

According to a further aspect, there is provided a method of making an apparatus comprising first and second sensor elements, the method comprising:

forming a first sensor element, the first sensor element comprising a first sensor material configured such that an electrical property of the first sensor material is dependent upon the temperature of the environment in which the first and second sensor elements are located; and forming a second sensor element, the second sensor element comprising a second sensor material configured such that the same electrical property of the second sensor material is dependent upon the relative vapour pressure of a fluid in the environment in which the first and second sensor elements are located, the respective temperature and fluid relative vapour pressure dependencies of the first and second sensor materials allowing the temperature and fluid relative vapour pressure of the environment to be determined based on combined measurements of the electrical property of the first and second sensor materials in the environment.

The steps of any method disclosed herein do not have to be performed in the exact order disclosed, unless explicitly stated or understood by the skilled person.

Corresponding computer programs (which may or may not be recorded on a carrier) for implementing one or more of the methods disclosed herein are also within the present disclosure and encompassed by one or more of the described example embodiments.

According to a further aspect, there is provided a computer program comprising computer code configured to determine the temperature and fluid relative vapour pressure of an environment using an apparatus, the apparatus comprising first and second sensor elements,
the first sensor element comprising a first sensor material and the second sensor element comprising a second sensor material, wherein the first sensor material is configured such that an electrical property of the first sensor material is dependent upon the temperature of the environment in which the first and second sensor elements are located, and the second sensor material is configured such that the same electrical property of the second sensor material is dependent upon the relative vapour pressure of a fluid in the environment in which the first and second sensor elements are located, the respective temperature and fluid relative vapour pressure dependencies of the first and second sensor materials allowing the temperature and fluid relative vapour pressure of the environment to be determined based on combined measurements of the electrical property of the first and second sensor materials in the environment, the computer code configured to measure the electrical property of the first and second sensor materials in the environment and determine the temperature and fluid relative vapour pressure of the environment based on the combined electrical property measurements.

The present disclosure includes one or more corresponding aspects, example embodiments or features in isolation or in various combinations whether or not specifically stated (including claimed) in that combination or in isolation. Corresponding means for performing one or more of the discussed functions are also within the present disclosure.

The above summary is intended to be merely exemplary and non-limiting.

BRIEF DESCRIPTION OF THE FIGURES

A description is now given, by way of example only, with reference to the accompanying drawings, in which:

FIG. 8b shows an interpenetrating spiral electrode geometry;

DESCRIPTION OF SPECIFIC ASPECTS/EMBODIMENTS

Figure 1A:
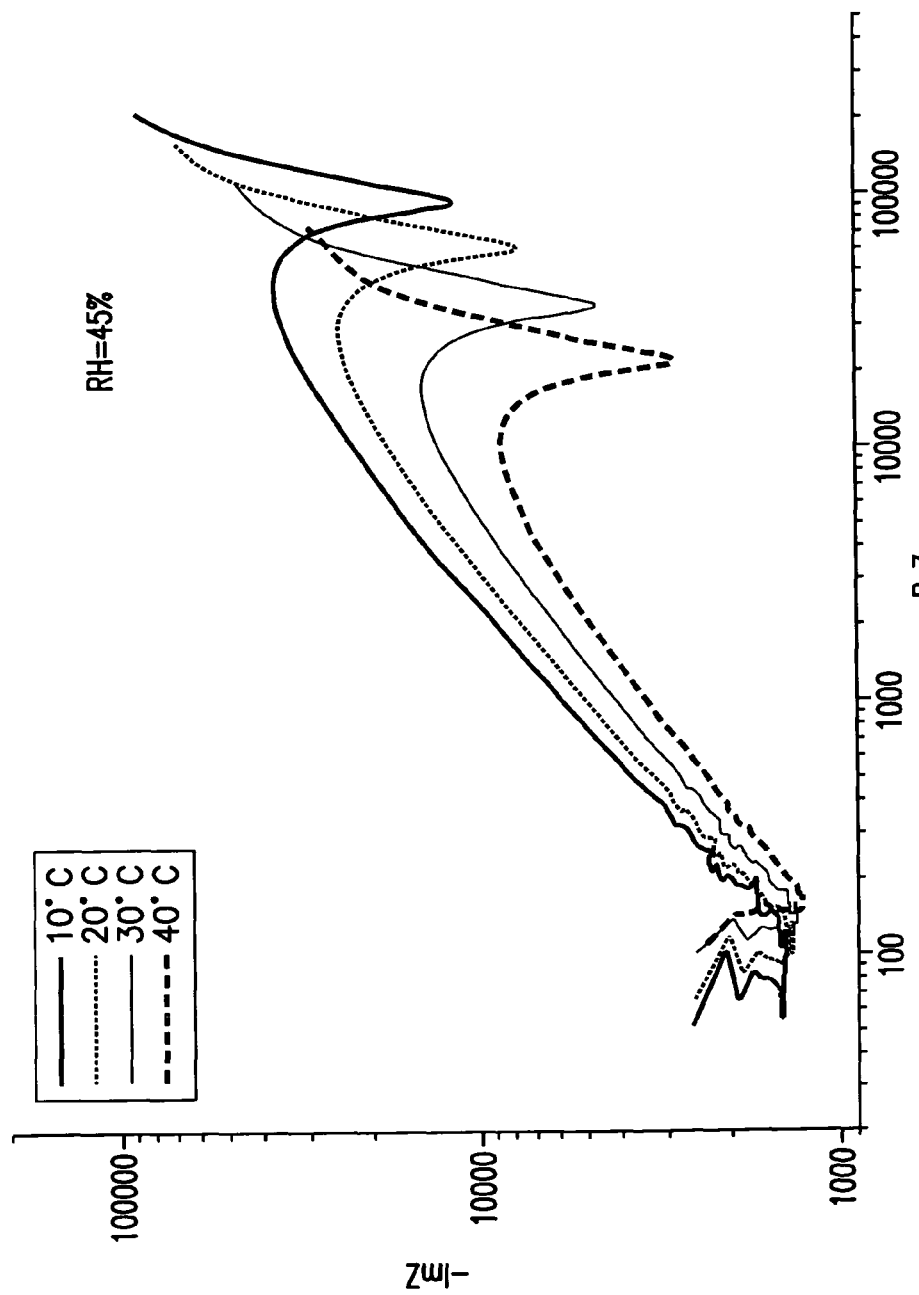
FIG. 1a shows impedance spectra (frequency range 40 Hz-110 MHz) of graphene oxide as a function of temperature.
Figure 1B:
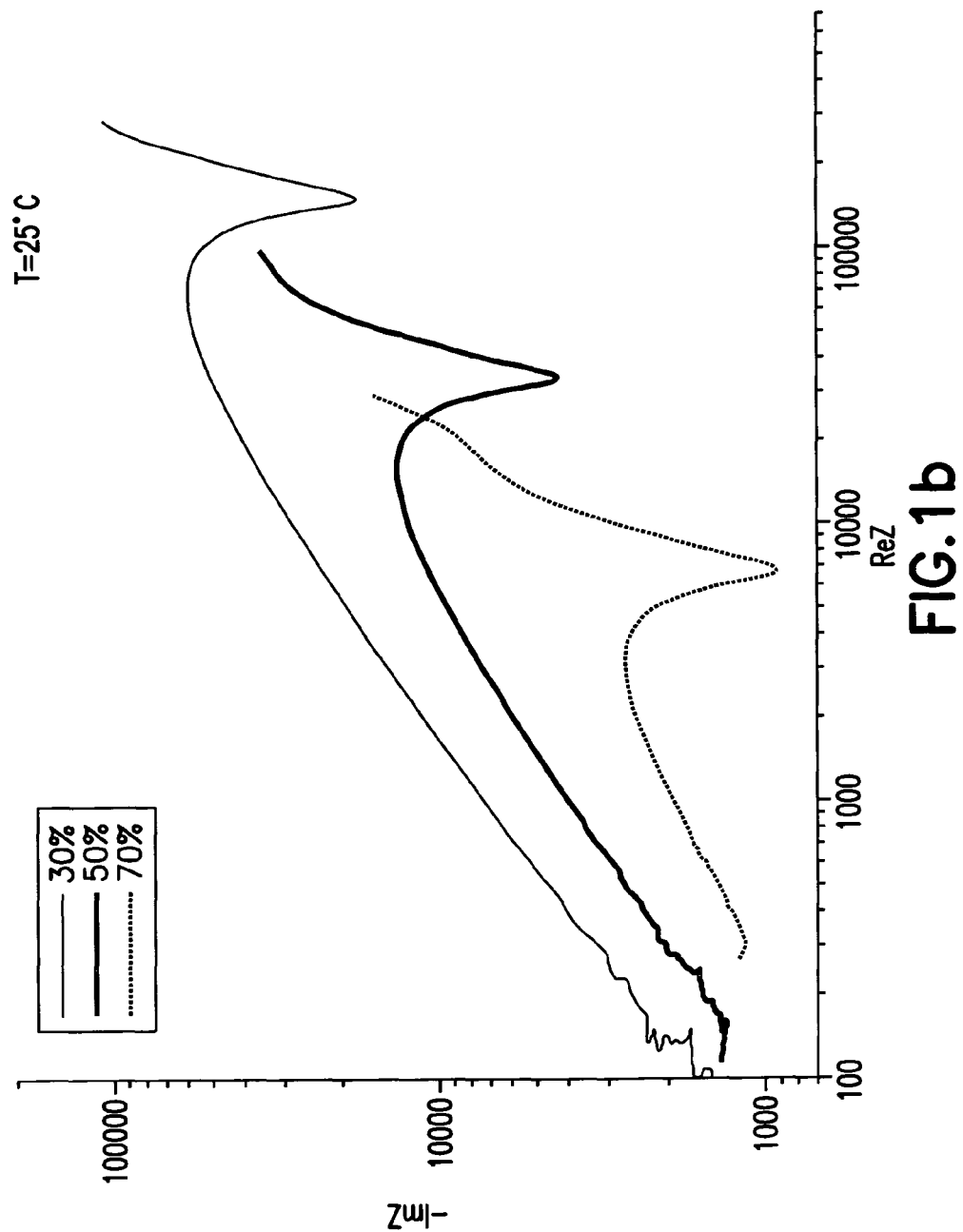
FIG. 1b shows impedance spectra (frequency range 40 Hz-110 MHz) of graphene oxide as a function of relative humidity.

The impedance of graphene oxide has been found to be exponentially dependent upon the temperature and relative humidity of the environment in which it is located. This is illustrated in FIGS. 1a and 1b which show complex impedance spectra of graphene oxide as a function of temperature (at a relative humidity of 45%) and relative humidity (at a temperature of 25° C.), respectively.

Figure 2:
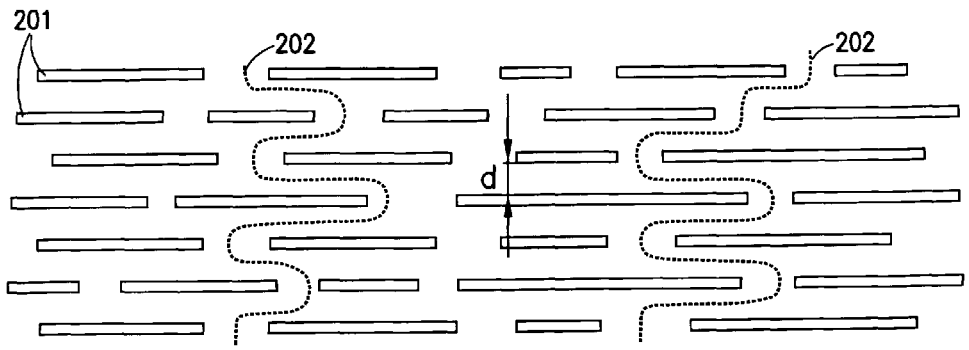
FIG. 2 shows water evaporation through a pseudo two-dimensional stack of graphene oxide platelets.
Figure 3:
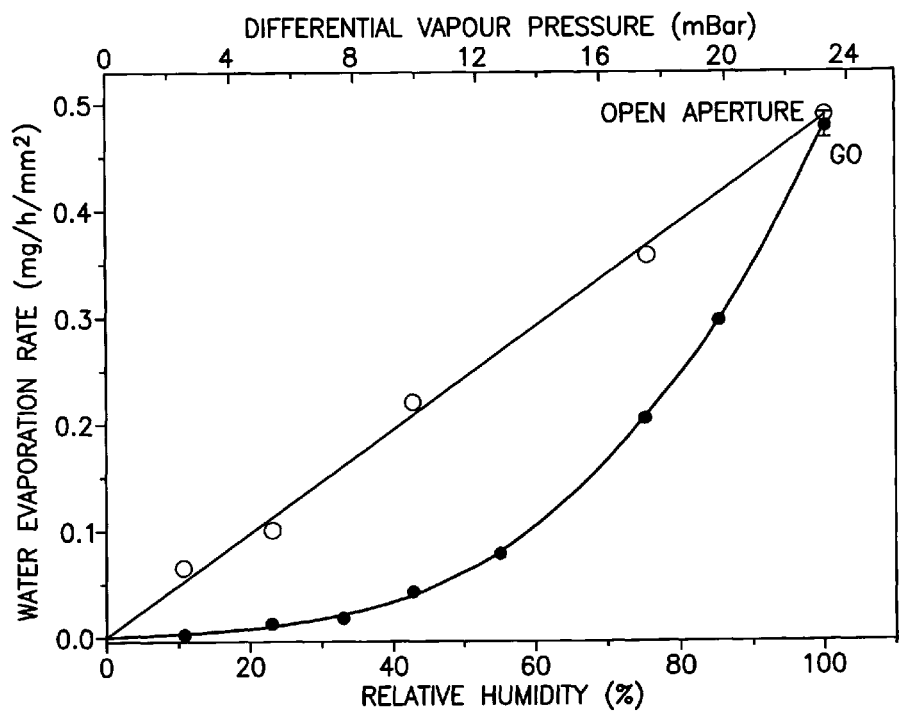
FIG. 3 shows the water permeation rate through an open aperture with and without a graphene oxide membrane as a function of relative humidity.

The temperature and humidity dependence is not fully understood, but may relate to the layered structure of the material. As shown in FIG. 2, graphene oxide comprises a stack of pseudo two-dimensional platelets 201 (with interstitial spacing "d") which allow the permeation of water 202 through the material. The permeation rate depends on both the temperature and relative humidity of the environment. FIG. 3 shows the rate of water evaporation through an open aperture and the same aperture covered with a 0.5 μm thick graphene oxide membrane. At 100% relative humidity, the water penetrates through the graphene oxide as though the membrane wasn't there. One possible explanation for this behaviour is that the relative humidity (and also the temperature) of the surrounding environment affect the interstitial spacing of the graphene oxide platelets, which in turn dictates the amount of water that can be absorbed by the material. When water fills the space between the platelets, the thickness of the material increases and charge transfer occurs between the water molecules and the graphene oxide resulting in the change in impedance.

The impedance of graphene oxide is also dependent upon the frequency (w) of the alternating current passing through the material. In Cartesian form, complex impedance (Z) is given by the expression $$Z = X - iY \quad \text{Equation 1}$$

where X is the real part of the impedance (i.e. the resistance) and Y is the imaginary part of the impedance (i.e. the reactance). In some ranges of temperature and humidity values, the dependence of the real and imaginary parts on frequency, temperature (T) and relative humidity (H) can be described by the following equations:

$$X(\omega,T,H) = F_X[\omega(T,H)] \cdot e^{-(\alpha T + \beta H)} \quad \text{Equation 2}$$

$$Y(\omega,T,H) = F_Y[\omega(T,H)] \cdot e^{-(\alpha T + \beta H)} \quad \text{Equation 3}$$

$$\omega(T,H) = \omega_0 e^{-(\alpha T + \beta H)} \quad \text{Equation 4}$$

where α and β are material-specific temperature and humidity coefficients.

As mentioned in the background section, low-cost integrated flexible temperature and humidity sensors are not currently available in the market. The apparatus and methods disclosed herein may or may not address this issue. Whilst the following discussion refers to the measurement of relative humidity, the present apparatus is not limited solely to the relative vapour pressure (e.g. concentration) of water vapour in the air. Rather, a suitably configured apparatus as described herein may be used to measure the relative vapour pressure of any fluid (which may comprise a liquid and/or gas) in the surrounding environment.

Figure 4:
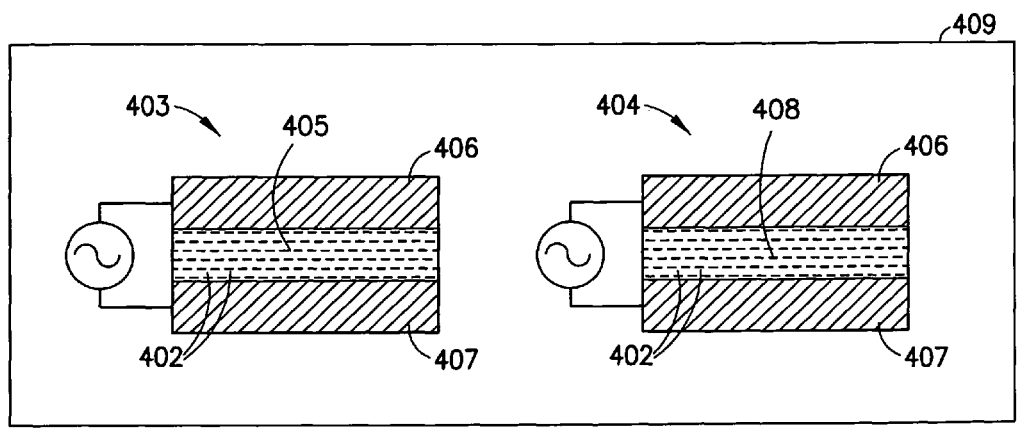
FIG. 4 shows first and second sensor elements according to one embodiment of the present disclosure.

As shown in FIG. 4, the present apparatus comprises first 403 and second 404 sensor elements. The first sensor element 403 comprises a first sensor material 405 and an electrode pair 406, 407 configured to enable a flow of alternating current through the first sensor material 405, and the second sensor element 404 comprises a second sensor material 408 and an electrode pair 406, 407 configured to enable a flow of alternating current through the second sensor material 408.

The first sensor material 405 is configured such that an electrical property of the first sensor material 405 (e.g. impedance, resistance, conductance, reactance and/or capacitance) is dependent upon the temperature of the environment 409 in which the first 403 and second 404 sensor elements are located, and the second sensor material 408 is configured such that the same electrical property of the second sensor material 408 is dependent upon the relative vapour pressure of a fluid (e.g. water) in the environment 409 in which the first 403 and second 404 sensor elements are located. The respective temperature and fluid relative vapour pressure dependencies of the first 405 and second 408 sensor materials allow the temperature and fluid relative vapour pressure (e.g. relative humidity) of the environment 409 to be determined based on combined measurements of the electrical property of the first 405 and second 408 sensor materials in the environment 409.

The electrical property of the first sensor material 405 may also be dependent upon the relative vapour pressure of the fluid in the environment 409, and the electrical property of the second sensor material 408 may also be dependent upon the temperature of the environment 409. In this scenario, however, the temperature and fluid relative vapour pressure dependencies of the first sensor material 405 (represented by the coefficients $\alpha_1$ and $\beta_1$, respectively) must be different from the temperature and fluid relative vapour pressure dependencies of the second sensor material 408 (represented by the coefficients $\alpha_2$ and $\beta_2$, respectively).

In practice, this may be achieved in a number of different ways. One method is to use different sensor materials 405, 408 for the first 403 and second 404 sensor elements. Like graphene oxide, each sensor material 405, 408 should comprise a stack of pseudo two-dimensional platelets to enable the absorption of fluid from the environment 409. Suitable materials include graphene, graphene oxide, reduced or partially reduced graphene oxide, boron nitride, fluorographene, hydrogenated graphene, tungsten disulphide, molybdenum disulphide, or any combination thereof. The first 405 and second 408 sensor materials may be selected such that the interstitial spacing of the pseudo two-dimensional platelets 402 in the first sensor material 405 is different from the interstitial spacing of the pseudo two-dimensional platelets 402 in the second sensor material 408 under the same environmental conditions.

Another option is to use the same oxide material 405, 408 (e.g. graphene oxide) for each sensor element 403, 404 but with different oxidation states. The level of oxidation can be controlled chemically, by laser irradiation or by other methods. This may be used to increase or decrease the penetration of fluid into the material 405, 408 (e.g. by changing the hydrophilicity of the material 405, 408), and/or to change the interaction of the material 405, 408 with the fluid, in order to adjust the temperature and humidity dependence. Additionally or alternatively, one or more functional groups may be added to the first sensor material 405 but not to the second sensor material 408, or different functional groups may be added to each sensor material 405, 408.

Another option is to use the same sensor material 405, 408 for the first and 403 and second 404 sensor elements but different electrode configurations (e.g. interdigitated comb electrodes, interpenetrating spiral electrodes or parallel plate electrodes) and/or different electrode materials for each sensor element 403, 404. For example, the use of silver electrodes 406, 407 for the first sensor element 403 and oxidised silver electrodes 406, 407 for the second sensor element 404 can result in the coefficients $\alpha_1$ and $\beta_1$ being different from the coefficients $\alpha_2$ and $\beta_2$.

Figure 5:
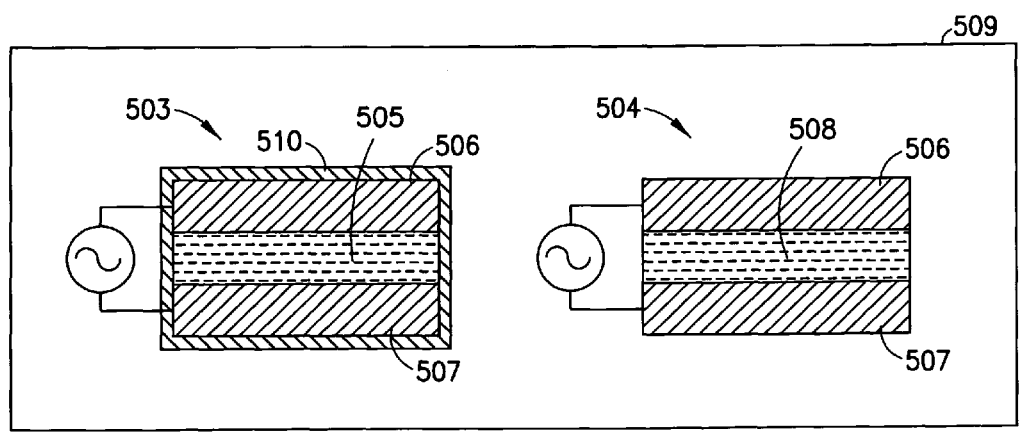
FIG. 5 shows first and second sensor elements according to another embodiment of the present disclosure.

A further option is to add a passivation layer 510 to one of the sensor elements 503, 504. This configuration is shown in FIG. 5, where the passivation layer 510 is added to the first sensor element 503 but not to the second sensor element 504. The passivation layer 510 may be formed from any material which prevents exposure of the sensor material 505 to the fluid in the environment 509. For example, when the fluid is water in the surrounding air, the passivation layer 510 may comprise a hydrophobic material (such as a fluoropolymer) to prevent such exposure. When a passivation layer 510 is added to one of the sensor elements 503, the electrical properties of the respective sensor material 505 become independent of the relative vapour pressure of fluid in the surrounding environment 509 (but still vary with temperature). As a result, the humidity coefficient ($\beta_1$) becomes zero for this sensor element 503.

Figure 13A:
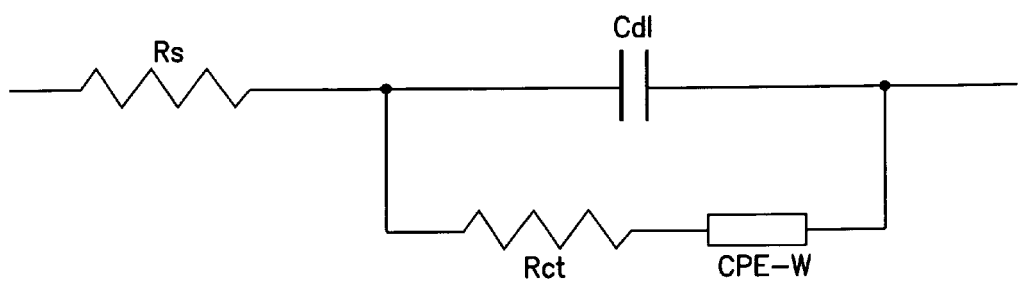
FIG. 13a shows an equivalent circuit used to represent a graphene oxide-based sensor element.

Before the apparatus can be used to measure the temperature and relative humidity of the environment 509, the temperature and humidity coefficients ($\alpha$, $\beta$) of each sensor material 505, 508 must be calculated. This may be done by modelling each sensor element 503, 504 as an equivalent circuit in which only two parameters vary as a function of temperature and relative humidity. The impedance spectrum of a graphene oxide film can be generally obtained by using the equivalent circuit shown in FIG. 13a. The equivalent circuit comprises a series resistance ($R_s$), a double-layer capacitance ($C_{dl}$), a charge transfer resistance ($R_{ct}$) and a constant phase element (CPE-W). Upon changing the temperature and/or relative humidity of the environment, only the charge transfer resistance and the constant phase element are affected. For example, within a range of temperature and relative humidity (e.g. 15° C.$\leq$T$\leq$45° C. and 0.3$\leq$H$\leq$0.8), the variation of charge transfer resistance can be described by the following equation:

$$\log(R_{ct}) = \log(R_0) + \alpha(T-T_0) + \beta(H-H_0) \quad \text{Equation 5}$$

where $R_0$ is the charge transfer resistance under reference conditions of temperature and humidity ($T_0$, $H_0$), and $R_{ct}$ is the charge transfer resistance under any other temperature and humidity conditions (T, H). A similar relationship applies to the constant phase element (CPE-W) of the equivalent circuit.

The temperature and humidity coefficients of each sensor element 503, 504 can therefore be determined by measuring the charge transfer resistance (or other parameter) in an environmentally-controlled chamber under three different environmental conditions ($T_0$, $H_0$), ($T_0$, $H_1$) and ($T_1$, $H_0$) and solving the resulting simultaneous equations. In practice, the values of the charge transfer resistance can be obtained by measuring the impedance spectrum and fitting it according to the equivalent circuit.

Once $\alpha_1$, $\beta_1$, $\alpha_2$ and $\beta_2$ are known, the temperature and relative humidity of the (external) environment 509 can then be measured by combining Equation 5 for the two sensor elements 503, 504 and solving the resulting equations:

$$(T-T_0) = \frac{1}{\alpha_2\beta_1 - \alpha_1\beta_2} \cdot \left[\beta_1 \log\left(\frac{R_{ct2}}{R_{02}}\right) - \beta_2 \log\left(\frac{R_{ct1}}{R_{01}}\right)\right] \quad \text{Equation 6}$$

$$(H-H_0) = \frac{1}{\alpha_1\beta_2 - \alpha_2\beta_1} \cdot \left[\alpha_1 \log\left(\frac{R_{ct2}}{R_{02}}\right) - \alpha_2 \log\left(\frac{R_{ct1}}{R_{01}}\right)\right] \quad \text{Equation 7}$$

where the subscripts "1" and "2" relate to the first 503 and second 504 sensor elements, respectively.

In the case of very thin graphene oxide films (e.g. having a thickness of less than 50 nm), the contribution of the constant phase element (CPE-W) in the equivalent circuit can be neglected. As a result, the impedance spectrum can be obtained from a simpler equivalent circuit (shown in FIG. 13b) comprising only the double-layer capacitance ($C_{dl}$) and charge transfer resistance ($R_{ct}$) in parallel. With this equivalent circuit, only the charge transfer resistance depends on temperature and relative humidity. As a result, the temperature and relative humidity can be evaluated without the need to fit the whole impedance spectrum according to the equivalent circuit of FIG. 13a. Rather, as the double-layer capacitance ($C_{dl}$) remains approximately constant with temperature and relative humidity, and the time constant of the sensor element ($R_{ct}C_{dl}$) is typically short (e.g. ~100 μs) compared to the measurement frequency, it is possible to measure the charge transfer resistance ($R_{ct}$) as part of a voltage divider or Wheatstone bridge circuit.

Figure 13B:
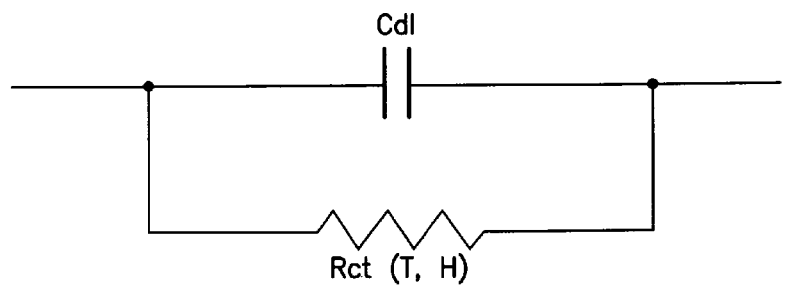
FIG. 13b shows an equivalent circuit used to represent a sensor element comprising a graphene oxide sensor material with a thickness of less than 50 nm.

In the case of thicker graphene oxide films (e.g. having a thickness of more than 50 nm), on the other hand, the contribution of the constant phase element (CPE-W) can be relevant for determining the impedance spectrum. Therefore, the simplified equivalent circuit of FIG. 13b is no longer applicable and the impedance spectrum must be fitted according to the equivalent circuit of FIG. 13a in order to obtain the values of charge transfer resistance ($R_{ct}$). Nevertheless, an alternative method can be used to exploit the impedance dependence of relatively thick graphene oxide films for sensing temperature and relative humidity.

When the impedance measurement is performed at a single frequency, the real (X) and imaginary (Y) parts of the impedance (Z) can be converted to an equivalent resistance ($R_p$) and capacitance ($C_p$) in parallel provided that Y<0. The resistance and capacitance are given by the following equations:

$$R_p = (1 + Q^2)X \quad \text{Equation 8}$$

$$C_p = \frac{1}{\omega\left(1 + \frac{1}{Q^2}\right)|Y|} \quad \text{Equation 9}$$

where Q=|Y|/X. Sensing of both temperature and relative humidity can be performed by measuring the impedance of first and second graphene oxide-based sensor elements at a given frequency and converting these measurements to a resistance ($R_p$) or capacitance ($C_p$) using Equations 8 and 9, respectively. In practice, the resistance ($R_p$) and capacitance ($C_p$) can be determined by measuring the impedance at a single frequency by means of a phase-sensitive detection (typically known as a lock-in measurement). The in-phase (X) and out-of-phase (Y) components of the impedance are obtained by mixing a copy of the drive signal with the measurement signal and applying a low-pass filter. This can be done by either analogue mixers, digital signal processing modules, or with software.

Figure 6A:
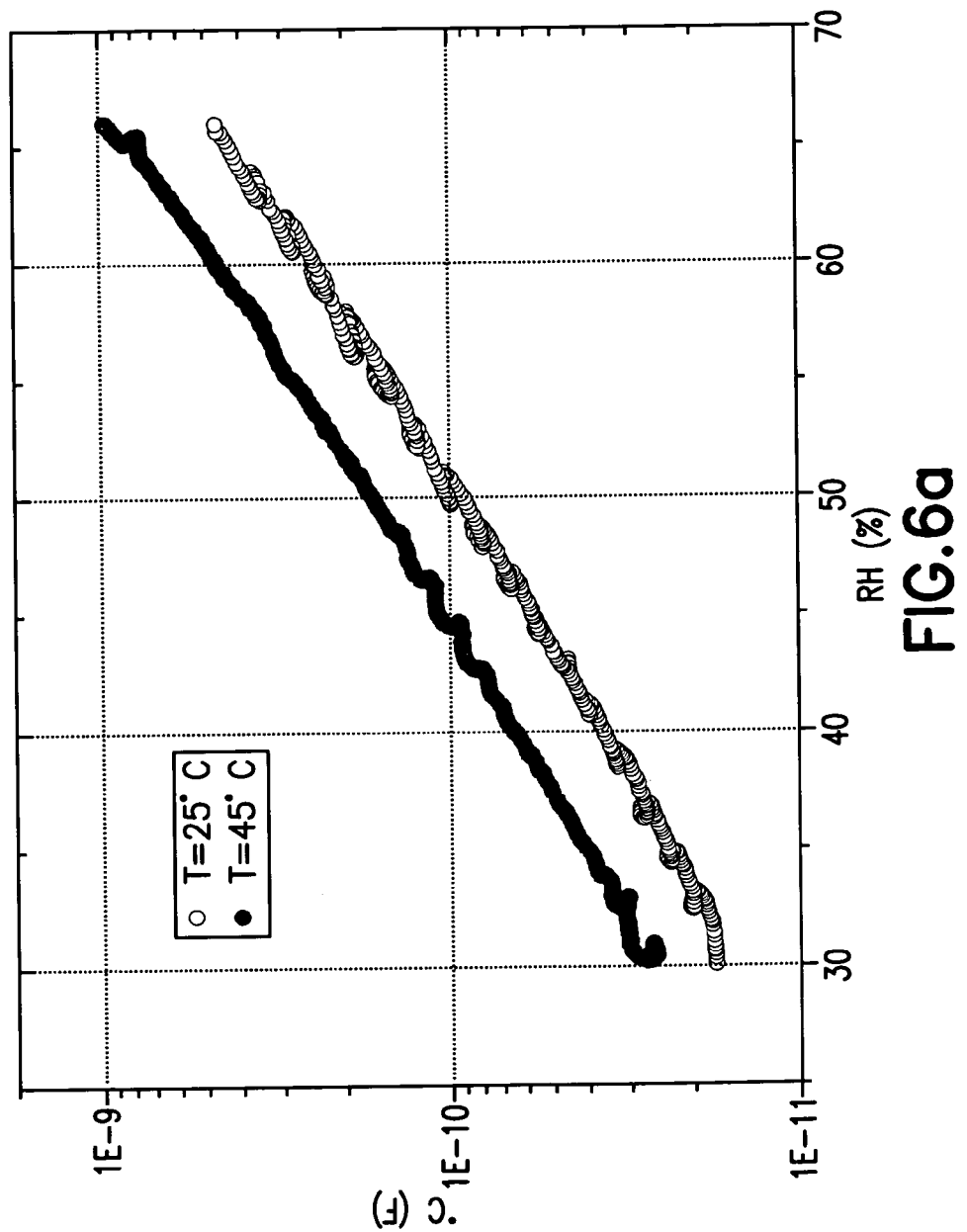
FIG. 6a shows the capacitance of graphene oxide as a function of relative humidity at two different temperatures.
Figure 6B:
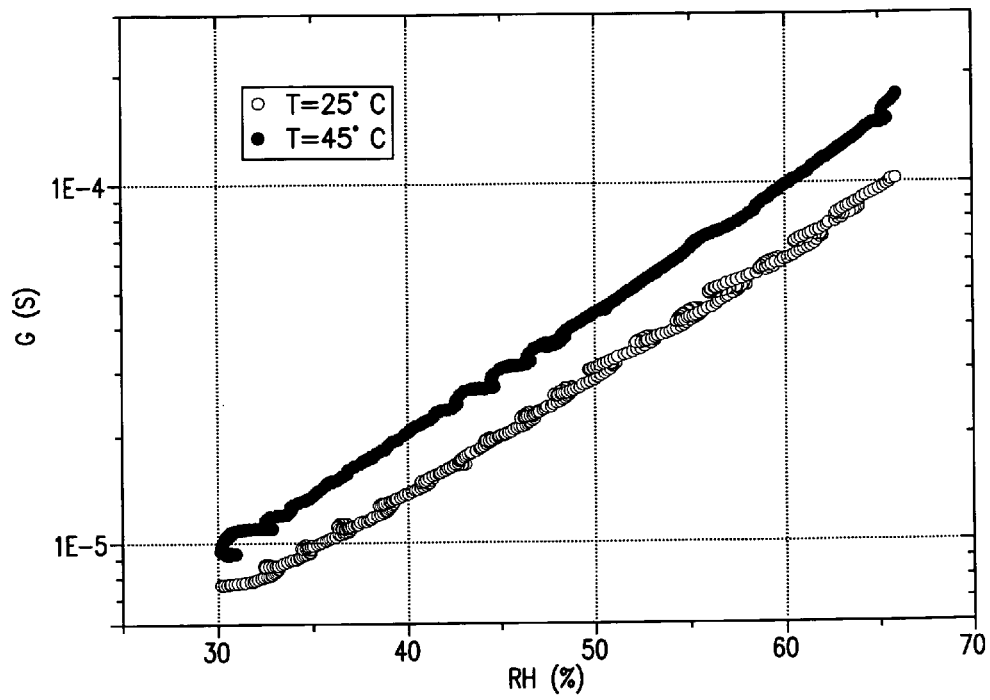
FIG. 6b shows the conductance of graphene oxide as a function of relative humidity at two different temperatures.

At certain frequencies of alternating current, the capacitance ($C_p$) of graphene oxide (and other materials) varies with temperature and relative humidity according to the following expression:

$$C_p = C_0(T)\exp\left[\frac{H}{x_0}\right] \quad \text{Equation 10}$$

where $C_0$ is a function of temperature referred to herein as the "pre-factor", and $x_0$ is a constant for a given frequency. The variation in capacitance with relative humidity at a frequency of 10 kHz is shown in FIG. 6a at 25° C. and 45° C. A similar relationship applies to the conductance ($G_p=1/R_p$) of graphene oxide, as shown in FIG. 6b. Therefore, monitoring the value of the capacitance or conductance of the first and second sensor elements at a given frequency is sufficient to obtain a measurement of temperature and relative humidity.

The relative humidity can be determined by rearranging Equation 10 as follows:

$$H = x_0 \ln\left[\frac{C_p}{C_0(T)}\right] \quad \text{Equation 11}$$

Before the apparatus can be used to measure the temperature and relative humidity of the environment 509, however, the pre-factor and constant must be determined. In this embodiment, the first sensor element 503 comprises a passivation layer 510 whilst the second sensor element 504 does not.

The constant can be found by measuring the capacitance of the second sensor material 508 in an environmentally-controlled chamber whilst varying the relative humidity at a constant temperature, and applying well-known linear regression techniques to the resulting capacitance vs humidity data. By keeping the temperature constant, any variation in the capacitance of the second sensor material 508 can be attributed to changes in relative humidity.

The next step is to measure the capacitance of the first sensor material 505 in the environmentally-controlled chamber whilst varying the temperature. The presence of the passivation layer 510 removes any humidity dependency from the first sensor material 505. The relationship between capacitance and temperature can then be determined from the capacitance vs temperature (calibration) data.

The temperature of the (external) environment 509 can be obtained by measuring the capacitance of the first sensor material 505 and comparing this value against the calibration data. Linear interpolation or extrapolation may be used to determine the temperature from any capacitance measurements that fall between the nodes in the calibration data. Once the temperature is known, the pre-factor can be calculated using the predetermined relationship from the calibration data.

Now that the constant and pre-factor have been determined, the relative humidity of the (external) environment 509 can be calculated by measuring the capacitance of the second sensor material 508 and using this value in Equation 11.

By using a passivation layer 510 in one of the sensor elements 503 and applying an alternating current at a frequency which produces a response as defined by Equation 10, the processing power and time associated with determining the temperature and relative humidity of the environment 509 can be reduced. This is because the temperature and humidity of the environment 509 can be measured directly using the first 503 and second 504 sensor elements (respectively) without the need to solve simultaneous equations.

In order to reduce the computational power associated with solving Equation 11 (since the exponential dependence of capacitance on relative humidity is not necessarily easy to calculate), the variation in capacitance of the second sensor material 508 with relative humidity could be measured in the environmentally-controlled chamber at a range of different temperatures and stored in a look-up table (i.e. resulting in a series of calibration data sets as shown in FIG. 6a). Once the temperature of the environment 509 is determined from the first sensor element 503, the relative humidity can be determined by measuring the capacitance of the second sensor material 508 and comparing it against the relevant data set in the look-up table. Linear interpolation or extrapolation may be used to determine the relative humidity from any capacitance measurements that fall between the nodes in the calibration data.

Figure 7:
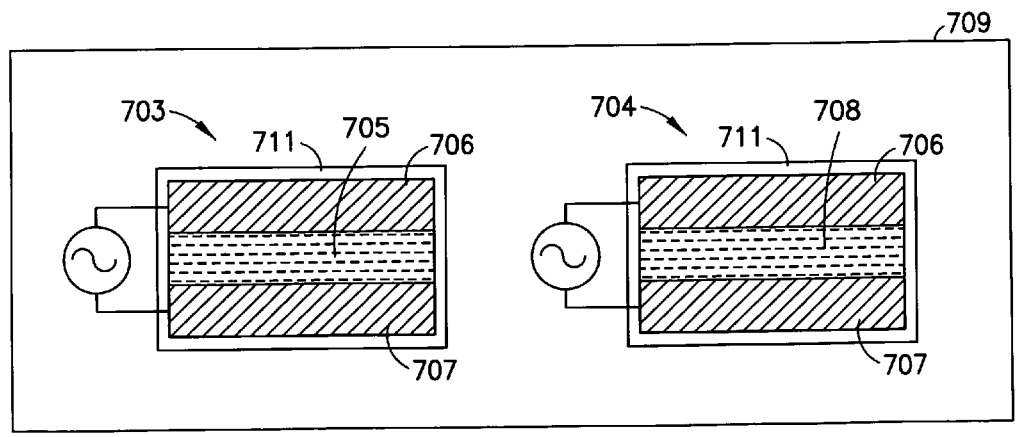
FIG. 7 shows first and second sensor elements according to another embodiment of the present disclosure.

As illustrated in FIG. 7, one or both of the first 703 and second 704 sensor elements may comprise a protective layer 711 configured to prevent damage to the first 705 and second 708 sensor materials, respectively. If the sensor element 703, 704 is configured to measure the relative vapour pressure of a fluid in the surrounding environment 709, the protective layer 711 should comprise a material (such as a block copolymer) which is permeable to the fluid to enable the prevention of damage to the sensor material 705, 708 without preventing the fluid relative vapour pressure of the environment 709 from being determined. On the other hand, if the sensor element 703, 704 is not configured to measure the relative vapour pressure of a fluid in the surrounding environment 709 (e.g. the first sensor element 503 in FIG. 5), the protective layer 711 may be configured to prevent exposure of the respective sensor material 705, 708 to the fluid. In this scenario, the protective layer 711 effectively doubles as a passivation layer 510.

FIG. 8 shows different electrode configurations which may be used with the present apparatus. As mentioned previously, the first 803 and second 804 sensor elements each comprise an electrode pair 806, 807 configured to enable a flow of alternating current through the respective sensor materials 805, 808. The electrode pair 806, 807 of the first 803 and/or second 804 sensor element may comprise interdigitated comb electrodes (FIG. 8a), interpenetrating spiral electrodes (FIG. 8b) or parallel plate electrodes (FIG. 8c).

Figure 8A:
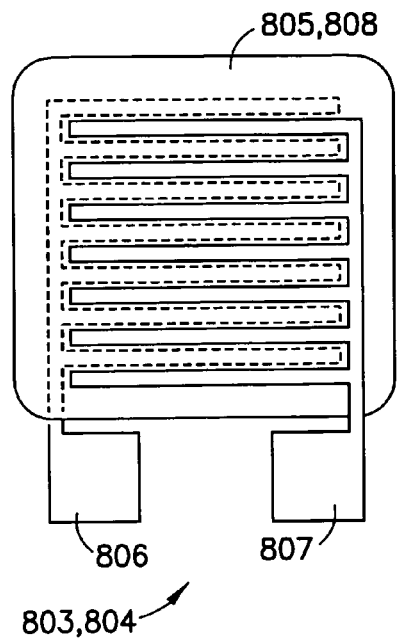
FIG. 8a shows an interdigitated comb electrode geometry.
Figure 8A:
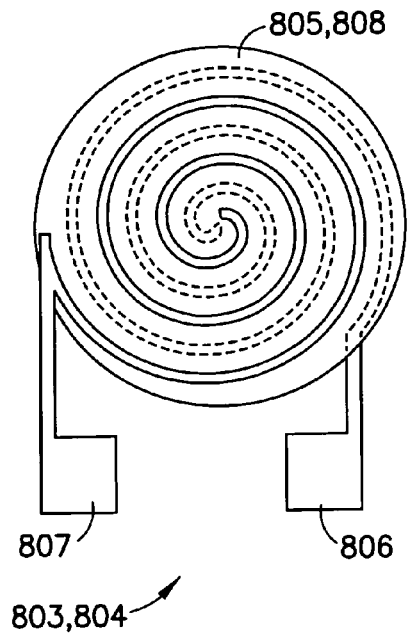
Figure 8C:
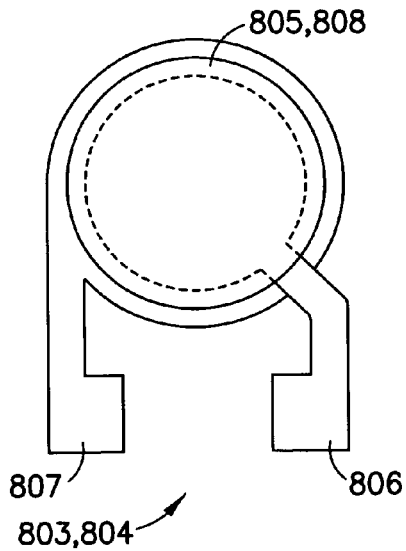
FIG. 8c shows a parallel plate electrode geometry.
Figure 8D:
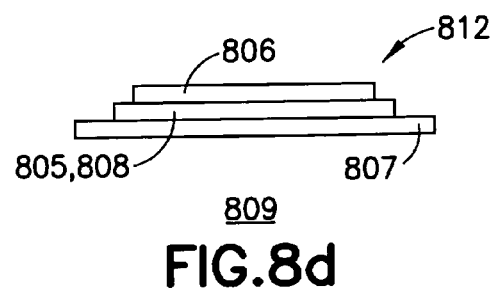
FIG. 8d shows the parallel plate electrode geometry of FIG. 8c in cross-section.

The affinity of the sensor material 805, 808 to the fluid in the environment 809 will influence the electrode configuration adopted. With the interdigitated comb and interpenetrating spiral configurations, both electrodes (i.e. the anode 806 and the cathode 807) of the electrode pair are formed on the same surface (typically the lower surface) of the sensor material 805, 808. This arrangement allows a greater surface area of the sensor material 805, 808 to interact with the environment 809 but results in a lower capacitance per unit area than the parallel plate configuration. With the parallel plate configuration, the sensor material 805, 808 is sandwiched between the two electrodes 806, 807 (as shown in FIG. 8*d*), resulting in a smaller amount of material 805, 808 being exposed to the surrounding environment 809 for interaction with the fluid. Despite the reduced surface area, however, the parallel plate configuration has been found to be suitable for use with graphene oxide. This is due to the high mobility of water molecules between the platelets of the material which allows water to access the material in the exposed region 812 at the periphery of the sensor element 803, 804. The higher capacitance per unit area associated with the parallel plate configuration facilitates the miniaturisation of the sensor elements 803, 804. The parallel plate configuration may also be suitable in the case of other materials for sensing different fluids.

When the first 803 and/or second 804 sensor element comprises a pair of parallel plate electrodes, one or both electrodes 806, 807 may be configured to serve as a passivation layer 510 and/or protective layer 711. This helps to reduce the number of material layers (and fabrication steps) required to form the apparatus. Additionally or alternatively, one or both electrodes 806, 807 may comprise a porous electrode material configured to enable diffusion of the fluid from the environment 809 to the sensor material 805, 806.

Figure 9:
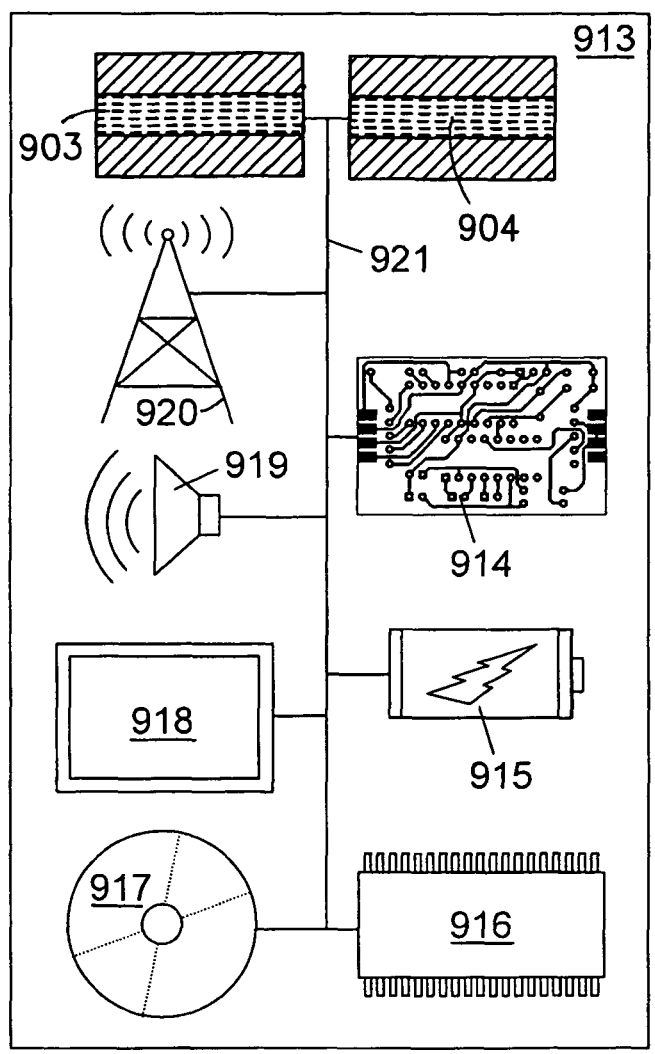
FIG. 9 shows an apparatus comprising the first and second sensor elements described herein.

FIG. 9 shows one example of the present apparatus. The apparatus may be one or more of an electronic device, a portable electronic device, a portable telecommunications device, a sensor, a wearable device, a wristband, a user interface for one or more of the same, an electronic display for one or more of the same, or a module for one or more of the same. When the apparatus is (or forms part of) a wearable device or wristband, some or all of the materials from which the apparatus is made may be flexible and/or stretchable (i.e. resilient materials).

In the example shown, the apparatus is an electronic device 913 comprising the first 903 and second 904 sensor elements described herein, an interface circuit 914, a battery 915, a processor/controller 916, a storage medium 917, an electronic display 918, a loudspeaker 919 and a transmitter 920, which are electrically connected to one another by a data bus 921.

As described previously, the first 903 and second 904 sensor elements are configured to allow the temperature and fluid relative vapour pressure of the environment to be determined based on combined measurements of an electrical property of the first and second sensor materials in the environment. Although only two sensor elements 903, 904 have been described in each of the examples provided herein, the apparatus 913 may comprise more than two sensor elements (but not less than two). The use of additional sensor elements can be used to increase the accuracy of the measurements and/or allow the relative vapour pressure of multiple fluids to be monitored simultaneously. For example, in the latter scenario, a third sensor element could be functionalised to detect a chemical vapour whilst the first 903 and second 904 sensor elements are being used to eliminate both the temperature and humidity dependencies.

The processor 916 is configured for general operation of the apparatus 913 by providing signalling to, and receiving signalling from, the other components to manage their operation. In addition, the processor 916 is configured to receive the electrical property measurements and perform the calculations described herein (e.g. using one or more algorithms stored on the storage medium 917) to determine the temperature and fluid relative vapour pressure of the environment.

The storage medium 917 is configured to store computer code configured to perform, control or enable operation of the apparatus 913. The storage medium 917 may also be configured to store settings for the other components. The processor 916 may access the storage medium 917 to retrieve the component settings in order to manage the operation of the other components. The storage medium 917 may also be configured to store temperature and/or humidity calibration data for one or both of the sensor elements 903, 904 for use by the processor 916 in determining the temperature and fluid relative vapour pressure of the environment.

The processor 916 may be a microprocessor, including an Application Specific Integrated Circuit (ASIC). The storage medium 917 may be a temporary storage medium such as a volatile random access memory. On the other hand, the storage medium 917 may be a permanent storage medium such as a hard disk drive, a flash memory, or a non-volatile random access memory.

The interface circuit 914 is configured to convert output signals from the first 903 and second 904 sensor elements into a form which is suitable for use by the processor 916. The interface circuit 914 may comprise a voltage divider, a Wheatstone bridge, a phase-sensitive detection circuit, or any other appropriate measurement circuit. The interface circuit 914 may also comprise appropriate amplifiers, buffers, filters, etc for matching the sensor response to the controller input, and/or an analogue-to-digital converter for converting the analogue sensor response into a digital signal for processing by a digital controller.

The electronic display 918 is configured to display the temperature and humidity of the environment to a user of the apparatus 913; the loudspeaker 919 is configured to output the temperature and humidity as an audio signal (i.e. sound) which is detectable by the user; and the transmitter 920 is configured to transmit the temperature and humidity (the final result and/or the raw data) to a remote apparatus such as the user's mobile phone. The transmitter 920 therefore allows the apparatus 913 to be positioned at a location which is remote from the user so that the user can monitor the temperature and humidity of the remote environment (e.g. via his/her mobile phone).

When the electrical property being measured is capacitance, the apparatus 913 may comprise one or more reference capacitors which can be switched to replace the first 903 and/or second 904 sensor elements. This allows the capacitance of the first and/or second sensor materials to be measured as a ratio to the capacitance of the reference capacitors, thereby eliminating any errors which might otherwise be introduced by the various components (e.g. due to amplifier drift or the like). Likewise, the apparatus 913 may comprise one or more reference resistors when the electrical property being measured is resistance.

Figure 10:
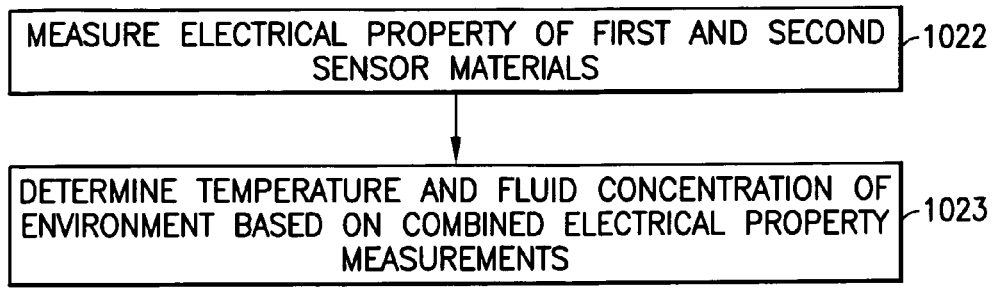
FIG. 10 shows the main steps of a method of determining the temperature and fluid relative vapour pressure of an environment using the apparatus of FIG. 9.
Figure 11:
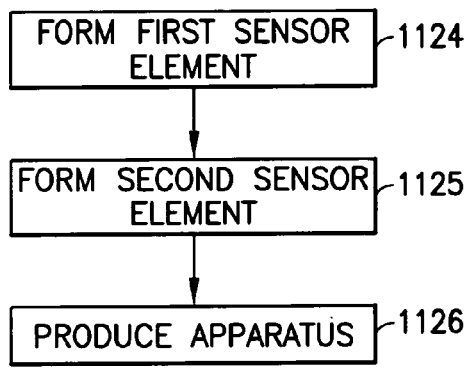
FIG. 11 shows the main steps of a method of making the apparatus of FIG. 9.

The main steps 1022-1023 of a method of determining the temperature and fluid relative vapour pressure of an environment using the present apparatus are illustrated schematically in FIG. 10. Similarly, the main steps 1124-1126 of a method of making the present apparatus are illustrated in FIG. 11. A number of different fabrication techniques may be used to produce the first and second sensor materials depending on the specific materials chosen. The following method may be used to form a thin film of graphene oxide.

Graphene oxide solution comprising graphene oxide platelets, water, organic solvents and stabilisers can be purchased from, for example, Graphene Square Inc. The solution can then be deposited on top of a substrate (such as PET or PEN) by spin coating, drop casting, spraying or inkjet printing, and the electrodes can be formed thereon using standard lithographic processes or printing techniques. Spin coating is useful for creating large homogeneous films of a few nanometers in thickness, whilst drop casting may be preferable if the sensor material is to be formed on a particular region of the substrate. Before the solution is deposited, the hydrophobicity of the substrate should be tuned to ensure wetability (in general, the more hydrophilic the substrate is, the more the solution will spread). This may be achieved by functionalisation or oxygen plasma treatment of the substrate surface. The thickness of the film can be controlled by the concentration and viscosity of the solution, as well as the spin speed if spin coating is used. After the solution has been deposited onto the substrate, the sample is left to allow the water and organic solvents to evaporate. A vacuum oven may be used to reduce the drying time, but can result in cracks in the film. Alternatively, the sample may be dried on a preheated roller under controlled environmental conditions to ensure fast evaporation of the water and organic solvents without the formation of cracks. The deposition and drying process may need to be repeated once or twice in order to form a pinhole-free film.

Figure 12:
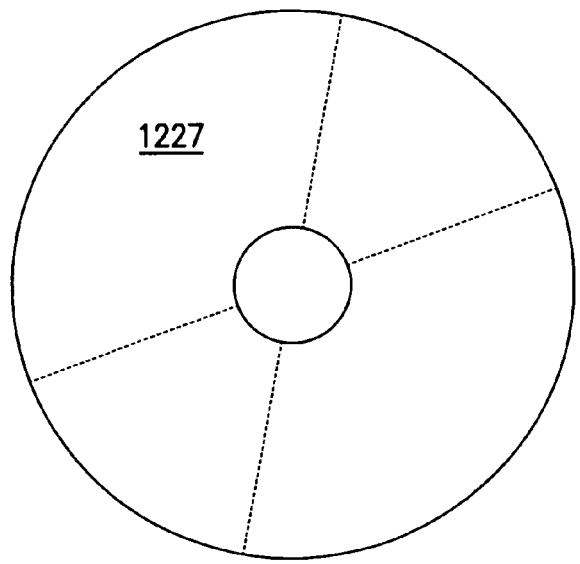
FIG. 12 shows a computer-readable medium comprising a computer program configured to perform, control or enable one or more of the method steps of FIGS. 10 and/or 11.

FIG. 12 illustrates schematically a computer/processor readable medium 1227 providing a computer program according to one embodiment. In this example, the computer/processor readable medium 1227 is a disc such as a digital versatile disc (DVD) or a compact disc (CD). In other embodiments, the computer/processor readable medium 1227 may be any medium that has been programmed in such a way as to carry out an inventive function. The computer/processor readable medium 1227 may be a removable memory device such as a memory stick or memory card (SD, mini SD, micro SD or nano SD).

The computer program may comprise computer code configured to perform, control or enable one or more of the method steps 1022-1023, 1124-1126 of FIG. 10 or 11. In particular, the computer program may be configured to measure the electrical property of the first and second sensor materials in the environment and determine the temperature and fluid relative vapour pressure of the environment based on the combined electrical property measurements.

Other embodiments depicted in the figures have been provided with reference numerals that correspond to similar features of earlier described embodiments. For example, feature number 1 can also correspond to numbers 101, 201, 301 etc. These numbered features may appear in the figures but may not have been directly referred to within the description of these particular embodiments. These have still been provided in the figures to aid understanding of the further embodiments, particularly in relation to the features of similar earlier described embodiments.

It will be appreciated to the skilled reader that any mentioned apparatus/device and/or other features of particular mentioned apparatus/device may be provided by apparatus arranged such that they become configured to carry out the desired operations only when enabled, e.g. switched on, or the like. In such cases, they may not necessarily have the appropriate software loaded into the active memory in the non-enabled (e.g. switched off state) and only load the appropriate software in the enabled (e.g. on state). The apparatus may comprise hardware circuitry and/or firmware. The apparatus may comprise software loaded onto memory. Such software/computer programs may be recorded on the same memory/processor/functional units and/or on one or more memories/processors/functional units.

In some embodiments, a particular mentioned apparatus/device may be pre-programmed with the appropriate software to carry out desired operations, and wherein the appropriate software can be enabled for use by a user downloading a "key", for example, to unlock/enable the software and its associated functionality. Advantages associated with such embodiments can include a reduced requirement to download data when further functionality is required for a device, and this can be useful in examples where a device is perceived to have sufficient capacity to store such pre-programmed software for functionality that may not be enabled by a user.

It will be appreciated that any mentioned apparatus/circuitry/elements/processor may have other functions in addition to the mentioned functions, and that these functions may be performed by the same apparatus/circuitry/elements/processor. One or more disclosed aspects may encompass the electronic distribution of associated computer programs and computer programs (which may be source/transport encoded) recorded on an appropriate carrier (e.g. memory, signal).

It will be appreciated that any "computer" described herein can comprise a collection of one or more individual processors/processing elements that may or may not be located on the same circuit board, or the same region/position of a circuit board or even the same device. In some embodiments one or more of any mentioned processors may be distributed over a plurality of devices. The same or different processor/processing elements may perform one or more functions described herein.

It will be appreciated that the term "signalling" may refer to one or more signals transmitted as a series of transmitted and/or received signals. The series of signals may comprise one, two, three, four or even more individual signal components or distinct signals to make up said signalling. Some or all of these individual signals may be transmitted/received simultaneously, in sequence, and/or such that they temporally overlap one another.

With reference to any discussion of any mentioned computer and/or processor and memory (e.g. including ROM, CD-ROM etc), these may comprise a computer processor, Application Specific Integrated Circuit (ASIC), field-programmable gate array (FPGA), and/or other hardware components that have been programmed in such a way to carry out the inventive function.

The applicant hereby discloses in isolation each individual feature described herein and any combination of two or more such features, to the extent that such features or combinations are capable of being carried out based on the present specification as a whole, in the light of the common general knowledge of a person skilled in the art, irrespective of whether such features or combinations of features solve any problems disclosed herein, and without limitation to the scope of the claims. The applicant indicates that the disclosed aspects/embodiments may consist of any such individual feature or combination of features. In view of the foregoing description it will be evident to a person skilled in the art that various modifications may be made within the scope of the disclosure.

While there have been shown and described and pointed out fundamental novel features as applied to different embodiments thereof, it will be understood that various omissions and substitutions and changes in the form and details of the devices and methods described may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment may be incorporated in any other disclosed or described or suggested form or embodiment as a general matter of design choice.

Furthermore, in the claims means-plus-function clauses are intended to cover the structures described herein as performing the recited function and not only structural equivalents, but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

The invention claimed is:

1. An apparatus comprising first and second sensor elements, the first sensor element comprising a first sensor material and the second sensor element comprising a second sensor material, wherein the first sensor material is configured such that an electrical property of the first sensor material is dependent upon the temperature of the environment in which the first and second sensor elements are located, and the second sensor material is configured such that the same electrical property of the second sensor material is dependent upon the relative vapour pressure of a fluid in the environment in which the first and second sensor elements are located, the respective temperature and fluid relative vapour pressure dependencies of the first and second sensor materials allowing the temperature and fluid relative vapour pressure of the environment to be determined based on combined measurements of the electrical property of the first and second sensor materials in the environment;

wherein the first sensor material is different from the second sensor material; and wherein the first and second sensor materials each comprise a stack of pseudo two-dimensional platelets having an interstitial spacing, and wherein the interstitial spacing of the pseudo two-dimensional platelets in the first sensor material is different from the interstitial spacing of the pseudo two-dimensional platelets in the second sensor material under the same environmental conditions.

2. The apparatus of claim 1, wherein the electrical property of the first sensor material is also dependent upon the relative vapour pressure of the fluid in the environment, and the electrical property of the second sensor material is also dependent upon the temperature of the environment.

3. The apparatus of claim 2, wherein the temperature and fluid relative vapour pressure dependencies of the first sensor material are different from the temperature and fluid relative vapour pressure dependencies of the second sensor material.

4. The apparatus of claim 1, wherein the first and second sensor materials each comprise oxide materials, and wherein the oxide material of the first sensor material has a different oxidation state than the oxide material of the second sensor material.

5. The apparatus of claim 1, wherein the first sensor material comprises one or more functional groups which are absent in the second sensor material.

6. The apparatus of claim 1, wherein the first and second sensor materials each comprise one or more functional groups, and wherein the one or more functional groups of the first sensor material are different to the one or more functional groups of the second sensor material.

7. The apparatus of claim 1, wherein the first sensor element comprises a passivation layer which is absent from the second sensor element, the passivation layer configured to prevent exposure of the first sensor material to the fluid in the environment.

8. The apparatus of claim 1, wherein the first and/or second sensor materials comprise one or more of graphene, graphene oxide, boron nitride, fluorographene, hydrogenated graphene, tungsten disulphide and molybdenum disulphide.

9. The apparatus of claim 1, wherein one or more of the first and second sensor elements comprise a protective layer configured to prevent damage to the first and second sensor materials, respectively, and wherein the protective layer comprises a material which is permeable to the fluid in the environment to enable the prevention of damage to the sensor material without preventing the fluid relative vapour pressure of the environment from being determined.

10. The apparatus of claim 1, wherein the first or second sensor elements comprise a protective layer configured to prevent damage to the first or second sensor material, respectively, and wherein the protective layer is configured to prevent exposure of the respective sensor material to the fluid in the environment.

11. The apparatus of claim 1, wherein the first and second sensor elements each comprise an electrode pair configured to enable a flow of alternating current through the respective sensor materials.

12. The apparatus of claim 11, wherein the electrode pair of the first sensor element comprises a different electrode geometry and/or electrode material from the electrode pair of the second sensor element.

13. The apparatus of claim 11, wherein the electrode pair of the first and/or second sensor elements comprises interdigitated comb electrodes, interpenetrating spiral electrodes or parallel plate electrodes.

14. The apparatus of claim 13, wherein one or both of the parallel plate electrodes of the first and/or second sensor element is configured to serve as a passivation layer and/or protective layer of the respective sensor element.

15. The apparatus of claim 1, wherein the apparatus is one or more of an electronic device, a portable electronic device, a portable telecommunications device, a sensor, a wearable device, a wristband, a user interface for one or more of the same, an electronic display for one or more of the same, and a module for one or more of the same.

16. A method of determining the temperature and fluid relative vapour pressure of an environment using an apparatus, the apparatus comprising first and second sensor elements, the first sensor element comprising a first sensor material and the second sensor element comprising a second sensor material, wherein the first sensor material is configured such that an electrical property of the first sensor material is dependent upon the temperature of the environment in which the first and second sensor elements are located, and the second sensor material is configured such that the same electrical property of the second sensor material is dependent upon the relative vapour pressure of a fluid in the environment in which the first and second sensor elements are located, the respective temperature and fluid relative vapour pressure dependencies of the first and second sensor materials allowing the temperature and fluid relative vapour pressure of the environment to be determined based on combined measurements of the electrical property of the first and second sensor materials in the environment, the method comprising measuring the electrical property of the first and second sensor materials and determining the temperature and fluid relative vapour pressure of the environment based on the combined electrical property measurements.

17. A computer program comprising computer code configured to determine the temperature and fluid relative vapour pressure of an environment using an apparatus, the apparatus comprising first and second sensor elements, the first sensor element comprising a first sensor material and the second sensor element comprising a second sensor material, wherein the first sensor material is configured such that an electrical property of the first sensor material is dependent upon the temperature of the environment in which the first and second sensor elements are located, and the second sensor material is configured such that the same electrical property of the second sensor material is dependent upon the relative vapour pressure of a fluid in the environment in which the first and second sensor elements are located, the respective temperature and fluid relative vapour pressure dependencies of the first and second sensor materials allowing the temperature and fluid relative vapour pressure of the environment to be determined based on combined measurements of the electrical property of the first and second sensor materials in the environment, the computer code configured to cause a measuring device to measure the electrical property of the first and second sensor materials in the environment and determine the temperature and fluid relative vapour pressure of the environment based on the combined electrical property measurements.

\* \* \* \* \*